United States Patent
Belalcazar

(10) Patent No.: US 8,983,592 B2
(45) Date of Patent: Mar. 17, 2015

(54) MONITORING FLUID IN A SUBJECT USING AN ELECTRODE CONFIGURATION PROVIDING NEGATIVE SENSITIVITY REGIONS

(75) Inventor: Andres Belalcazar, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1023 days.

(21) Appl. No.: 12/621,984

(22) Filed: Nov. 19, 2009

(65) Prior Publication Data

US 2010/0063412 A1 Mar. 11, 2010

Related U.S. Application Data

(63) Continuation of application No. 11/419,123, filed on May 18, 2006, now Pat. No. 7,640,056.

(51) Int. Cl.
- A61B 5/05 (2006.01)
- A61B 5/053 (2006.01)
- A61B 5/00 (2006.01)

(52) U.S. Cl.
CPC .............. *A61B 5/0537* (2013.01); *A61B 5/4869* (2013.01)
USPC ....................................................... 600/547

(58) Field of Classification Search
USPC ....................................................... 600/547
See application file for complete search history.

(56) References Cited

U.S. PATENT DOCUMENTS

| | | | |
|---|---|---|---|
| 5,732,710 A * | 3/1998 | Rabinovich et al. .......... | 600/547 |
| 5,957,861 A | 9/1999 | Combs et al. | |
| 6,370,424 B1 | 4/2002 | Prutchi | |
| 6,595,927 B2 | 7/2003 | Pitts-Crick et al. | |
| 7,184,821 B2 | 2/2007 | Belalcazar et al. | |
| 7,640,056 B2 | 12/2009 | Belalcazar | |
| 2003/0028221 A1 | 2/2003 | Zhu et al. | |
| 2004/0102712 A1 | 5/2004 | Belalcazar et al. | |
| 2004/0172080 A1 | 9/2004 | Stadler et al. | |
| 2005/0043767 A1 | 2/2005 | Belalcazar | |
| 2005/0124908 A1 | 6/2005 | Belalcazar et al. | |
| 2005/0215918 A1 | 9/2005 | Frantz et al. | |
| 2005/0245992 A1 | 11/2005 | Persen et al. | |
| 2006/0184060 A1 | 8/2006 | Belalcazar et al. | |
| 2007/0282185 A1 | 12/2007 | Belalcazar | |

OTHER PUBLICATIONS

"U.S. Appl. No. 11/149,123, Supplemental Response filed Jul. 15, 2008 to Office Action mailed Apr. 7, 2008", 10 pgs.
"U.S. Appl. No. 11/149,123, Supplemental Response filed Sep. 30, 2008 to Office Action mailed Jul. 15, 2008", 8 pgs.
"U.S. Appl. No. 11/419,123, Response filed Apr. 7, 2008 to Non-Final Office Action mailed Jan. 7, 2008", 12 pgs.

(Continued)

*Primary Examiner* — Lee S Cohen
*Assistant Examiner* — Emily Lloyd
(74) *Attorney, Agent, or Firm* — Schwegman Lundberg & Woessner, P.A.

(57) ABSTRACT

An amount of fluid in a thoracic or other region of a subject may be monitored by internally injecting an electrical energy stimulus (e.g., constant voltage source) through the region, detecting voltage resulting from the electrical energy stimulus, and calculating a fluid volume indicative signal. The injected energy stimulus creates a first lead field. The responsive voltage is detected using an electrode configuration that defines a second lead field, which is arranged in a negative sensitivity configuration with respect to the first lead field at the region being monitored.

19 Claims, 7 Drawing Sheets

(56) References Cited

OTHER PUBLICATIONS

"U.S. Appl. No. 11/419,123, Non-Final Office Action mailed Jan. 7, 2008", 13 pgs.

"U.S. Appl. No. 11/419,123, Final Office Action mailed Dec. 12, 2008.", 17 pgs.

"U.S. Appl. No. 11/419,123, Non Final Office Action mailed Mar. 31, 2009", 19 pgs.

"U.S. Appl. No. 11/419,123, Notice of Allowance mailed Aug. 24, 2009", 8 Pgs.

"U.S. Appl. No. 11/419,123, Response filed Jul. 31, 2009 to Non Final Office Action mailed Mar. 31, 2009", 12 pgs.

"U.S. Appl. No. 11/419,123, Response filed Mar. 12, 2009 to Final Office Action mailed Dec. 12, 2008", 13 pages.

Belalcazar, A., et al., "Monitoring Lung Edema Using the Pacemaker Pulse and Skin Electrodes", *Physiol. Meas.*, 26, (2005), S153-S163.

Dudley, Jr., S. C., et al., "Reversal of Low Voltage and Infarction Pattern on the Surface Electrocardiogram After Renal Hemodialysis for Pulmonary Edema", *Journal of Electrocardiology*, 23(4), (Oct. 1990), 341-345.

Malmivuo, J., et al., "Table of Contents", *Bioeletromagnetism—Principals and Applications of Bioeletric and Biomagnetic Fields*, Oxford University Press, New York, NY, (1995), 11 pgs.

Kauppinen, P. K, et al., "Lead field theoretical approach in bioimpedance measurements: towards more controlled measurement sensitivity", Ann N Y Acad Sci., 873, (Apr. 20, 1999), 135-42.

\* cited by examiner

US 8,983,592 B2

MONITORING FLUID IN A SUBJECT USING AN ELECTRODE CONFIGURATION PROVIDING NEGATIVE SENSITIVITY REGIONS

CROSS REFERENCE TO RELATED APPLICATION

This application is a continuation of U.S. application Ser. No. 11/419,123, filed May 18, 2006, now issued as U.S. Pat. No. 7,640,056 which is hereby incorporated by reference in its entirety.

TECHNICAL FIELD

This patent document pertains generally to measuring an amount of fluid in a region of a subject, such as the thoracic region. More particularly, but not by way of limitation, this patent document pertains to monitoring fluid in a region of a subject using an electrode configuration with negative sensitivity and methods related thereto.

BACKGROUND

Variations in how much fluid is present in a subject's thoracic region can take various forms and can have different causes. As one example, eating salty foods can result in the retainment of excessive fluid in the thorax, which is commonly referred to as "thoracic fluid," and elsewhere. Another source of fluid build-up in the thorax is pulmonary edema, which involves a build-up of extravascular fluid in or around the lungs.

One cause of pulmonary edema is congestive heart failure (referred to as "CHF"), which is also sometimes referred to as "chronic heart failure," or simply as "heart failure." CHF may be conceptualized as an enlarged weakened heart muscle. The impaired heart muscle results in poor cardiac output of blood. As a result of such poor blood circulation, blood tends to pool in blood vessels in the lungs and becomes a barrier to normal oxygen exchange. In brief, pulmonary edema may be an indicative and important condition associated with CHF.

Pulmonary edema, if it exists, may present a medical emergency that requires immediate care. While it can sometimes prove fatal, the outlook for subjects possessing pulmonary edema can be good upon early detection and prompt treatment of the same. If left undetected (and consequently untreated), pulmonary edema may lead to death.

BRIEF DESCRIPTION OF THE DRAWINGS

In the drawings, which are not necessarily drawn to scale, like numerals describe substantially similar components throughout the several views. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the present systems and methods may be practiced. These embodiments, which are also referred to herein as "examples," are described in enough detail to enable those skilled in the art to practice the present systems and methods. The embodiments may be combined, other embodiments may be utilized or structural, electrical, or logical changes may be made without departing from the scope of the present systems and methods. The following detailed description is, therefore, not to be taken in a limiting sense, and the scope of the present systems and methods are defined by the appended claims and their legal equivalents.

In this document, the terms "a" or "an" are used to include one or more than one; the term "or" is used to refer to a nonexclusive "or" unless otherwise indicated; the term "subject" is used to include the term "patient"; and the term "thorax" refers generally to a subject's body between the neck and the diaphragm. In addition, it is to be understood that the phraseology or terminology employed herein, and not otherwise defined, is for the purpose of description only and not of limitation.

Furthermore, in the event of inconsistent usages between this document and those documents so incorporated by reference, the usage in the incorporated references should be considered supplementary to that of this document; for irreconcilable inconsistencies, the usage in this document controls.

Introduction

In general, edema (i.e., an excess fluid buildup in a region of a subject) is a failure or decompensation of one or more homeostatic processes within a subject's body. The body normally prevents the build-up of fluids therewithin by maintaining adequate pressures and concentrations of salt and proteins, and by actively removing excess fluid. If a disease affects any of these normal bodily mechanisms or if the normal bodily mechanisms are unable to keep up with the fluid build-up, the result may be edema, such as pulmonary edema.

Figure 1:
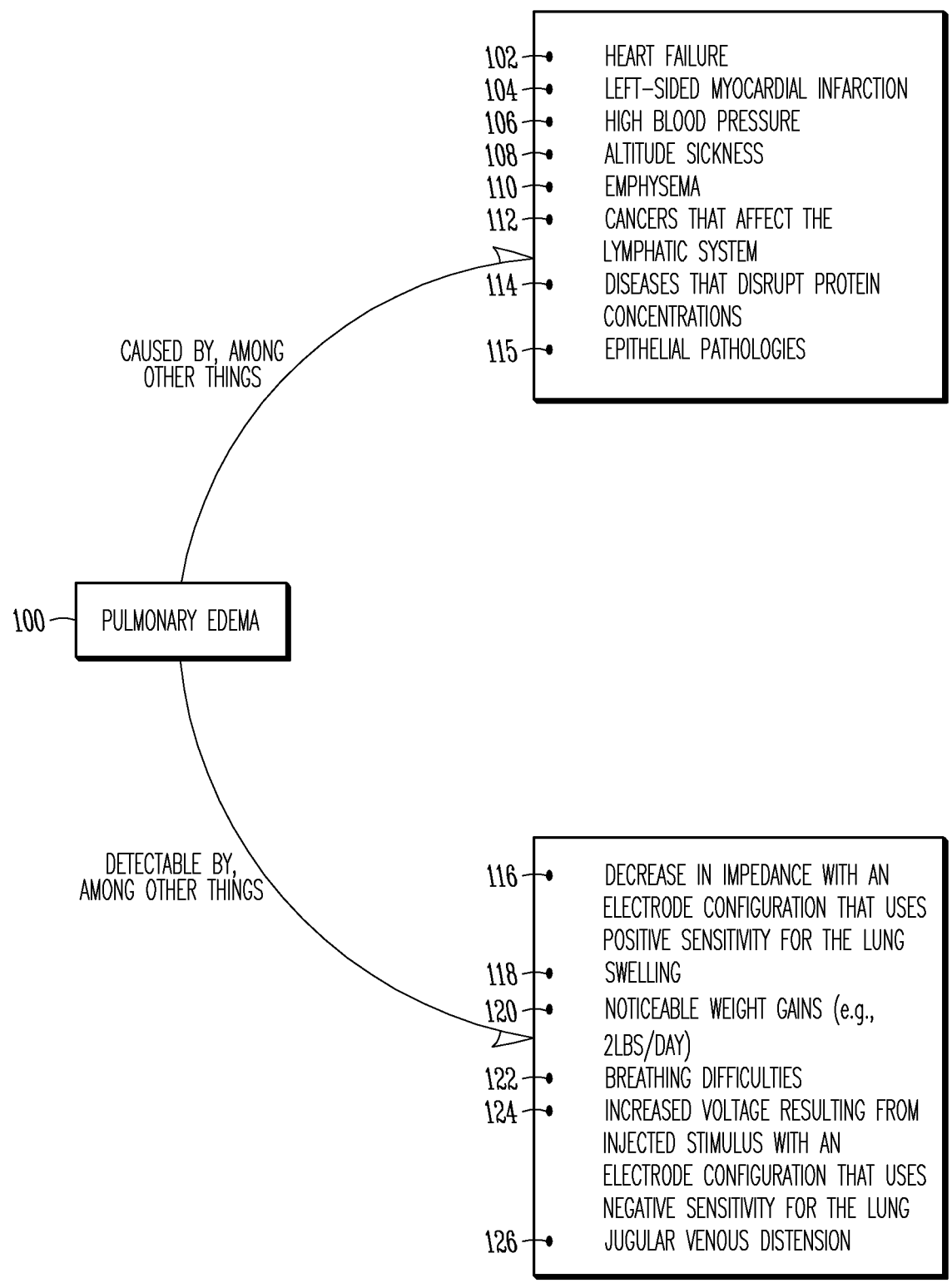
FIG. 1 is a block diagram illustrating exemplary causes and indications of abnormal fluid build-up in a subject's lungs, such as may be the result of pulmonary edema.

There are several conditions or diseases that may cause or affect pulmonary edema. As shown in FIG. 1, this includes, among others, heart failure 102, left-sided myocardial infarction 104, high blood pressure 106, altitude sickness 108, emphysema 110, cancers that affect the lymphatic system 112, diseases that disrupt protein concentrations 114, or epithelial pathologies 115, such as those caused by inhalation of toxic chemicals, leading to flooding of the alveoli. While pulmonary edema 100 may be a sign of many conditions or diseases, the prospect that pulmonary edema 100 may be a sign of failing heart circulation is often of first concern to caregivers (e.g., health care professionals) due to the severity of its nature.

Unfortunately, the first indication that an attending caregiver typically has of an occurrence of pulmonary edema 100 is very late in the disease process, such as when it becomes a physical manifestation with swelling 118, noticeable weight gains 120, jugular venous distension 126, or breathing difficulties 122 so overwhelming as to be noticed by the subject who then proceeds to be examined by his/her caregiver. For a heart failure subject, hospitalization at such a (physically apparent) time would likely be required.

Today, heart failure is a major cause of hospital admissions. A portion of these admissions is due to fluid accumulation in the lungs as a result of pulmonary edema 100, which is challenging to treat and often goes unrecognized until a subject is critically ill. It is not unusual for subjects with heart failure to require hospitalization or urgent treatment at an emergency room or critical care unit. It is estimated that approximately 30-40% of subjects with heart failure are hospitalized every year. Further, heart failure is a leading diagnosis-related group among hospitalized subjects over the age of 65.

Morbidity and mortality of heart failure can potentially be lowered with timely detection and appropriate treatment of disease conditions in their early stages, such as upon early detection and treatment of pulmonary edema 100. Early detection and treatment of pulmonary edema 100 may reduce or eliminate the need for hospital admission of subjects with heart failure. A reduction or elimination of the need for hospitalization results in lower health care costs. It is currently estimated that overall expenditures for management and treatment of heart failure may be as high as 24 billion dollars or more per year.

In an effort to detect impending edema and avoid its associated hospitalizations, the present systems and methods utilize concepts of lead field theory. In brief, a lead field can be used to describe a current density vector field that results when a unit of current is applied between at least two electrodes. "Lead field" is a concept that applies to the electrodes injecting current ("current lead field") as well as to those electrodes measuring resulting voltage ("voltage lead field"). Although a lead field associated with the voltage measurement electrodes may seem surprising at first, as voltage measurement does not entail the injection of current and therefore the creation of an associated lead field in the body, it is sometimes convenient to theoretically conceptualize a current density field resulting from energizing the voltage measurement electrodes with a unit of current.

In designing electric systems that monitor fluid via tissue resistivity changes, it is useful to arrange electrodes in the body so that the current and voltage lead fields intersect at a targeted region with desired geometries and orientations. This allows for high sensitivity in a particular organ (e.g., the lung) or simplification of the circuitry of a monitoring system, thereby potentially reducing its cost. It is possible to arrange the electrodes to create regions within a subject that have positive sensitivity. In a positive sensitivity region, an increase in fluid results in a corresponding decrease in the monitored voltage and impedance. It is also possible to arrange the electrodes to create regions within the subject that have negative sensitivity, in which an increase in fluid results in an increase in the monitored voltage and impedance.

The negativity or positivity of sensitivity in the monitored region is a characteristic of the dot product of the current and voltage lead fields at the desired region's location. For example, in a four electrode system with two electrodes injecting a test current and two other electrodes measuring a resulting voltage, if the current and voltage lead fields have opposing directions (e.g., an angle between the lead field lines is greater than 90 degrees) at the region of interest, such region will be a negative sensitivity region (see, e.g., FIG. 4, where the left lung 304 is located in a region of negative sensitivity). On the other hand, if the fields are parallel or substantially parallel (e.g., an angle between the lead field lines is less than 90 degrees), then the region will have positive sensitivity (see, e.g., FIG. 3, where the left lung 304 is located in a positive sensitivity region).

With the above discussed lead theory in mind, the present systems and methods may advantageously provide enhanced detection of pulmonary edema 100 (FIG. 1) or other abnormal fluid build-up, such as by providing increased sensitivity or by providing more simple monitoring, which may be less costly to implement. This may provide a more timely or cheaper indication of heart failure. As one example, increased fluid within a subject may be monitored using an increase in a measured voltage resulting from an internally injected electrical energy stimulus 124 (FIG. 1) (e.g., a constant voltage source given by, for example, a leading edge part of a capacitor discharge pacing pulse) when electrodes are arranged such that the lung or other region of interest is substantially located in a negative sensitivity region.

EXAMPLES

Positive Sensitivity

As discussed in commonly assigned Belalcazar, U.S. patent application No. Ser. No. 11/419,120, entitled "MONITORING FLUID IN A SUBJECT USING A WEIGHT SCALE," filed May 18, 2006, which is hereby incorporated by reference in its entirety, it is possible to monitor fluid in a thoracic region 302 (FIG. 3) by making one or more electrical impedance measurements across a subject's lungs 304 (FIG. 3) (such measurements commonly referred to as "thoracic impedance"). One exemplary technique for measuring thoracic impedance includes, among other things, internally injecting a (typically constant) current through thoracic region 302 using an implantable medical device (referred to as "IMD") 306 (FIG. 3) having at least one electrode associated therewith, detecting a resulting voltage using one or both of IMD 306 or an external device having at least one other electrode associated therewith. This measurement may be carried out in a manner such that the lead fields associated with the current injection electrodes and resulting voltage measurement electrodes are substantially parallel at the organ being targeted for monitoring. An impedance value can be calculated by taking the ratio of resulting voltage to injected current. That is, the thoracic impedance (Z) may be determined from Ohm's law (Z=resulting voltage/injected current).

Figure 2:
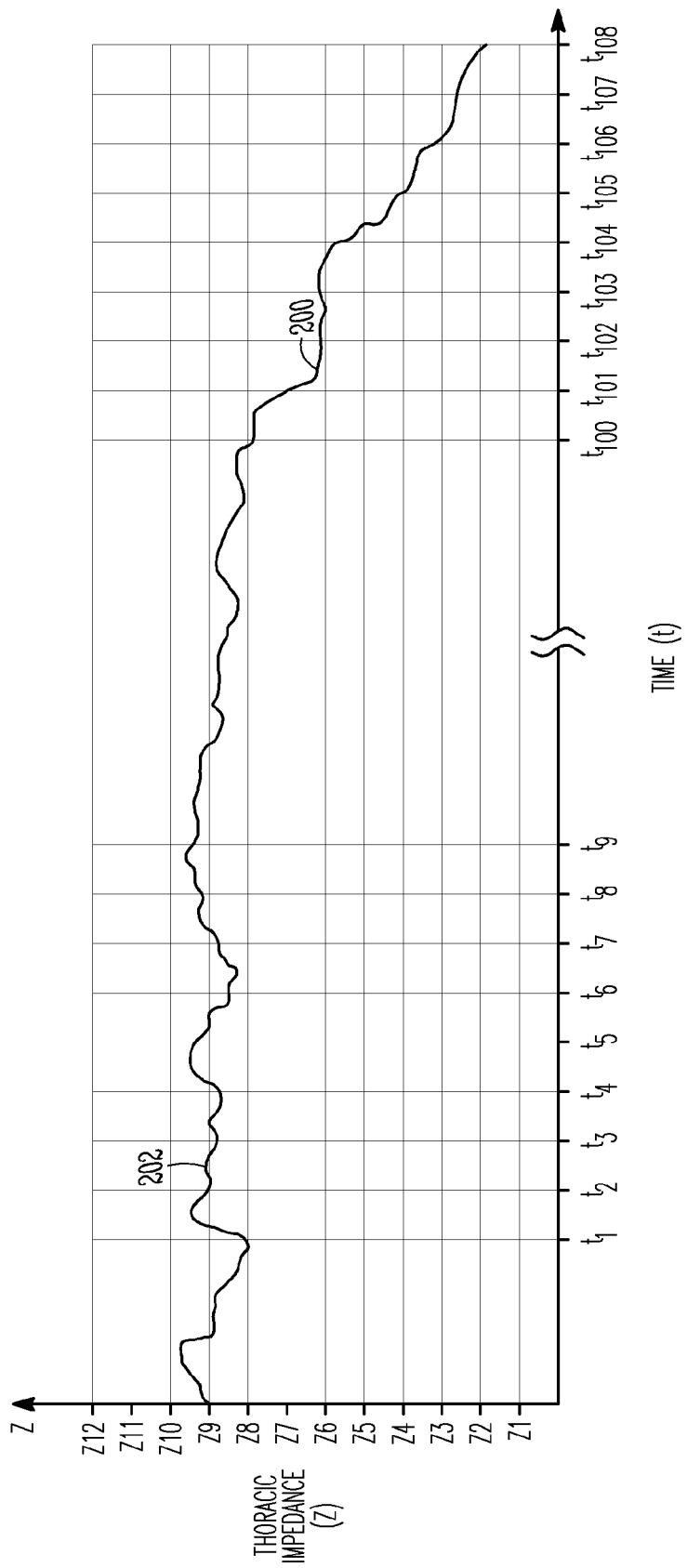
FIG. 2 is a graph illustrating a trend in calculated thoracic impedance that may indicate an increased fluid build-up in a subject's lungs or other organ.
Figure 3:
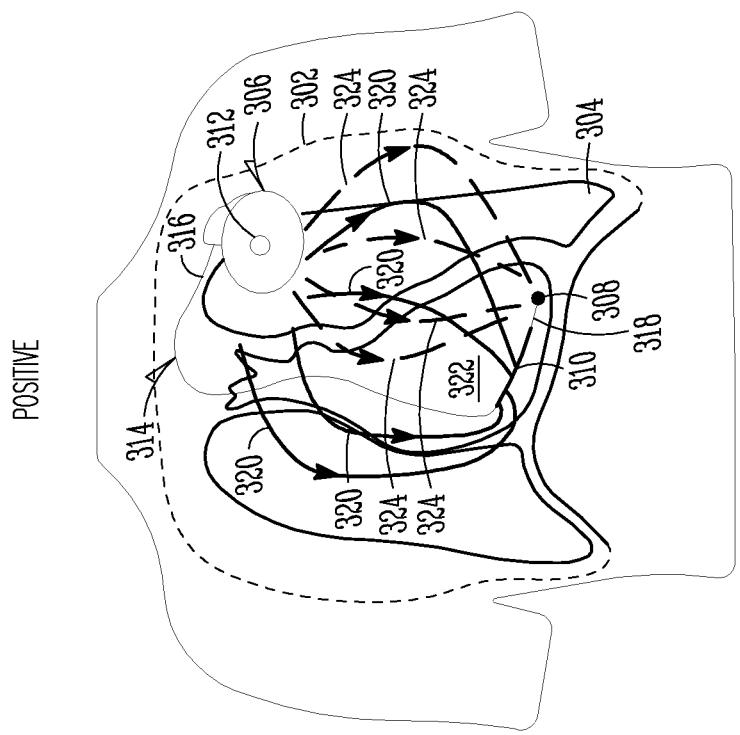
FIG. 3 is a perspective view illustrating at least a portion of an exemplary system adapted to monitor thoracic fluid in a subject, the system including an electrode configuration providing positive sensitivity regions within the subject.

Because internal organs, such as left lung 304, have electrical resistance, electric field laws predict that a flow of current (e.g., injected current) will result in a voltage across the organs in a subject. As fluid content in the organ increases, the resistivity of the organ decreases, and, for a given current, the resulting voltage also decreases. As a result of the voltage decreasing, thoracic impedance 116 will also decrease. In this way, a reduction in thoracic impedance 116 indicates the presence of an increase in fluid within an organ, such as the lungs 304 (FIG. 3). Conversely, a fluid decrease in the lungs 304 corresponds to an increase in thoracic impedance sensed. FIG. 2 illustrates a general decrease 200 in thoracic impedance (Z) as time progresses, such as from time period $t_{100}$-$t_{108}$, and thereby indicates an increase in fluid in the thoracic cavity during such period, which may be the result of pulmonary edema 100. Initially, such as from time period $t_0$-$t_9$, FIG. 2 illustrates a substantially stable fluid balance condition as the thoracic impedance trends horizontally 202.

FIG. 3 shows an example of an electrode configuration with positive sensitivity with respect to a subject's left lung 304, that yields such an antagonistic relationship between resulting voltage and injected current. In such a system, the magnitude of the current and voltage tend in opposite directions with an increase in left lung 304 fluid. In FIG. 3, associated lead fields substantially align with one another at the left lung (i.e., intersect at angles less than 90 degrees). In this example, an implantable apparatus including an IMD 306 and at least one lead 314 electrically coupled thereto are shown within a cut-away area of a subject. The at least one lead 314 extends from a lead proximal end 316, where it is coupled to IMD 306, to a lead distal end 318 disposed within, over, or about a heart 322 and thereby provides at least one conductive path from IMD 306 to heart 322. As shown, but as may vary, the at least one lead 314 includes two implanted electrodes 308, 310 disposed near lead distal end 318, while a housing 312 or header portion of the IMD 306 acts as a third implanted electrode by being at least partially conductive (typically referred to as a "can" electrode).

In this way, when IMD 306 provides an electrical energy stimulus (provided by, for example, a dedicated constant current source circuit), lead 314 and one of electrodes 308 or 310 deliver the stimulus through one or more internal organs as an injected current, which may return to the IMD 306 by way of conductive housing 312. As shown, a lead field 320 is associated with the current-injecting electrodes. The injected current results in a voltage being created, such voltage being measurable using the other one of electrodes 308 or 310 together with the housing electrode 312. As shown, a lead field 324 is associated with the resulting voltage measurement electrodes.

In traditional impedance systems which use positive sensitivity arrangements, what is sought with electrode positioning is to maximize at the target organ the so-called "dot product" of the current and voltage lead fields. In the example of FIG. 3, the electrodes associated with the electrical energy stimulus (i.e., the injected current) define a first lead field in the thoracic region, while the electrodes associated with the resulting voltage define a second lead field. In placing the electrodes optimally, one may seek to increase the dot product in the organ of interest, such as by decreasing the angle of intersection between vectors of the current and voltage lead fields. Increasing the magnitudes of the current and voltage lead fields in the organ or region of interest will also tend to increase the dot product at that organ. The current and voltage lead fields depend on the electrode positioning as well as on the internal distribution and properties of tissues. As shown in FIG. 3, the lead field associated with the electrical energy stimulus electrodes 310, 312 and the lead field associated with the resulting voltage measurement electrodes 308, 312 are in a similar orientation and approximately parallel, and therefore, tend to maximize the dot product in the region around heart 322 and left lung 304. Due to the parallel same-orientation nature of the associated fields at the left lung, such an electrode configuration may be referred to as an electrode arrangement with positive sensitivity with respect to the left lung 304.

Negative Sensitivity

The dot product at a given thoracic region can also be negative, and therefore, so can the sensitivity of the monitoring system to that region. A negative dot product, and thus a negative sensitivity, occurs in regions (e.g., 406 (FIG. 4)) where the field vectors (e.g., 402, 404 (FIG. 4)) associated with the electrical energy stimulus electrodes and the resulting voltage measurement electrodes have components in opposite directions (e.g., where the lead fields intersect at angles greater than 90 degrees). In regions with negative sensitivity, an increase in fluid decreases tissue resistivity, but will actually cause an increased voltage and impedance. That is, in a negative sensitivity arrangement with a constant voltage source, for example, injected current and measured voltage change synergistically with an increase in fluid (as opposed to antagonistically, such as in a positive sensitivity arrangement). Therefore, it is actually detrimental to use impedance in this case, as taking the ratio of voltage to current will actually diminish the resulting physiological signal. Computer modeling indicates that, in a negative sensitivity arrangement, delivering a constant test voltage and monitoring a resulting voltage is sufficient for fluid monitoring.

Figure 4:
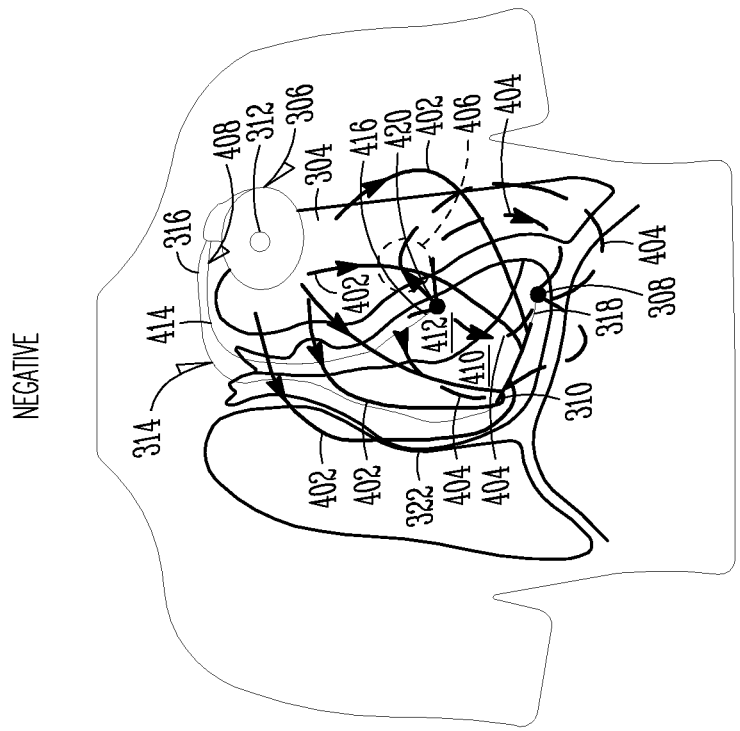
FIG. 4 is a perspective view illustrating at least a portion of an exemplary system adapted to monitor thoracic fluid in a subject, the system including an electrode configuration providing negative sensitivity regions within the subject.

FIG. 4 illustrates one exemplary negative sensitivity electrode arrangement having associated lead fields that substantially oppose one another at the left lung 304. In this example, an implantable apparatus includes an IMD 306, a first lead 314, and a second lead 408. First lead 314 extends from a lead proximal end 316, where it is coupled to IMD 306, to a lead distal end 318 disposed within, over, or about a heart 322 (such as a right ventricle 410) and thereby provides at least one conductive path from IMD 306 to the right ventricle. Second lead 408 extends from a lead proximal end 414 to a lead distal end 416 disposed within, over, or about heart 322 (such as a left ventricle 412) and thereby provides a conductive path from IMD 306 to the left ventricle. As shown, but as may vary, first lead 314 includes two (implanted) electrodes 308, 310 disposed near lead distal end 318, second lead 408 includes one (implanted) electrode 420 disposed near lead distal end 416, and a housing 312 or header of IMD 306 acts as a fourth (implanted) can electrode by being conductive or at least partial conductive.

In this way, when IMD 306 provides an electrical energy stimulus (e.g., from a constant voltage source given by, for example, a leading edge part of an applied pacing pulse via electrical energy output circuit 602 (FIG. 6)), lead 314 and electrode 310 deliver the stimulus through one or more internal organs as an injected current, which may return to the IMD by way of conductive housing 312. As shown, a lead field 402 is associated with the electrical energy stimulus electrodes. The electrical energy stimulus results in a responsive voltage measured (i.e., sensed) using electrodes 308 and 420. As shown, a lead field 404 is associated with the resulting voltage measurement electrodes. As further shown in FIG. 4, the lead field associated with the electrical energy stimulus electrodes 310, 312 and the lead field associated with the resulting voltage measurement electrodes 420, 308 have substantially opposite directions at the left lung 304, and thus illustrate a negative sensitivity electrode arrangement for that target organ.

Figure 5:
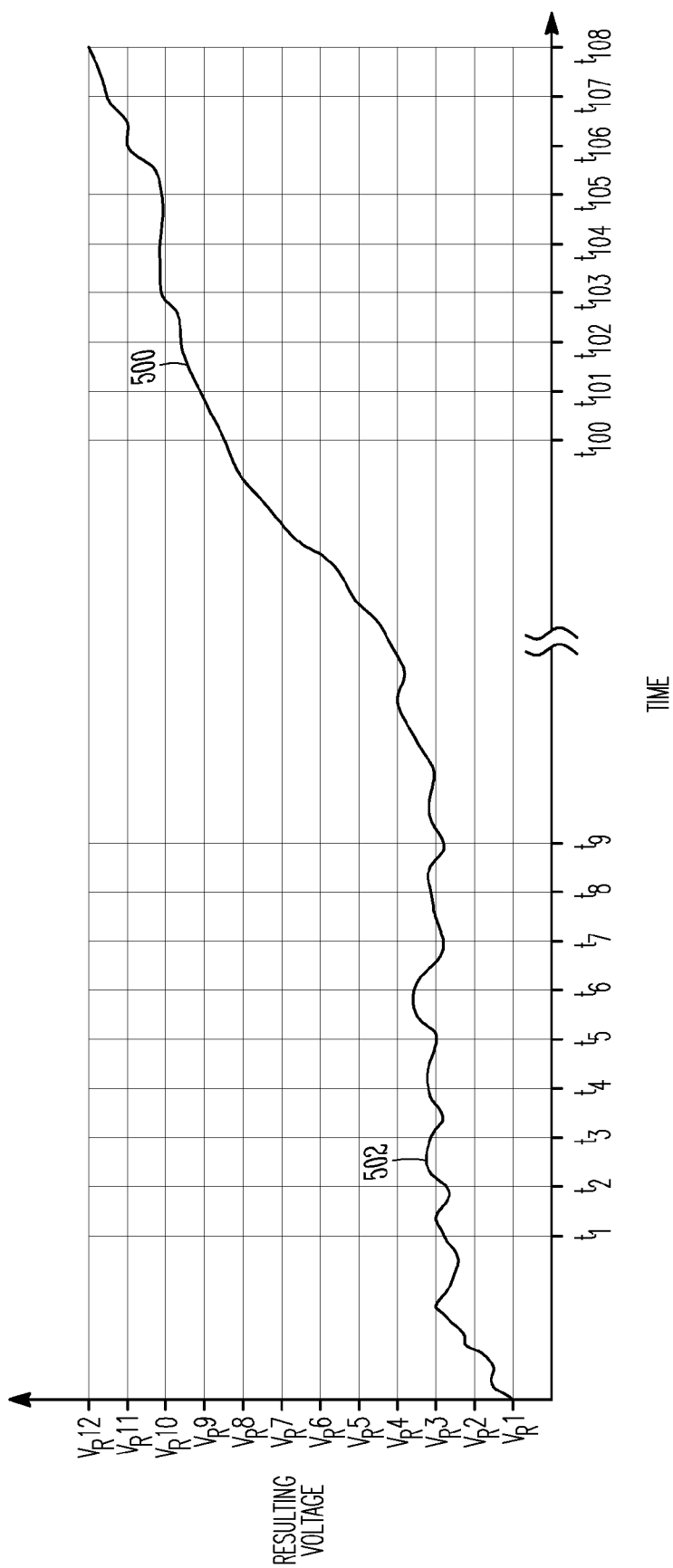
FIG. 5 is a graph illustrating a trend in sensed voltage resulting from an injected stimulus that may indicate an increased fluid build-up in a subject's lungs.

In brief, the lead fields associated with the electrode configuration of FIG. 4 negatively intersect in a left lung 304 (see, e.g., phantom encapsulated region 406). Accordingly, when using a constant voltage source, for example, to inject current, a sensed increase in resulting voltage indicates an increase in fluid within such region. The constant voltage source may be implemented as the leading edge of a cardiac or other stimulation pulse derived from discharging a capacitor into the body. In such an arrangement, impedance is not required to monitor fluid within a region of a subject. Rather, more simply, delivering a constant test voltage and monitoring of a resulting voltage changes on the sensing electrodes may be used. FIG. 5 illustrates a general increase 500 in resulting voltage ($V_R$) as time progresses, such as from time period $t_{100}$-$t_{108}$, and thereby (in a negative sensitivity arrangement) indicates an increase in fluid in the thoracic cavity during such period, which may be the result of pulmonary edema 100. Initially, such as from time period $t_0$-$t_9$, FIG. 5 illustrates a substantially stable fluid balance condition as the resulting voltage trends horizontally 502.

Figure 6:
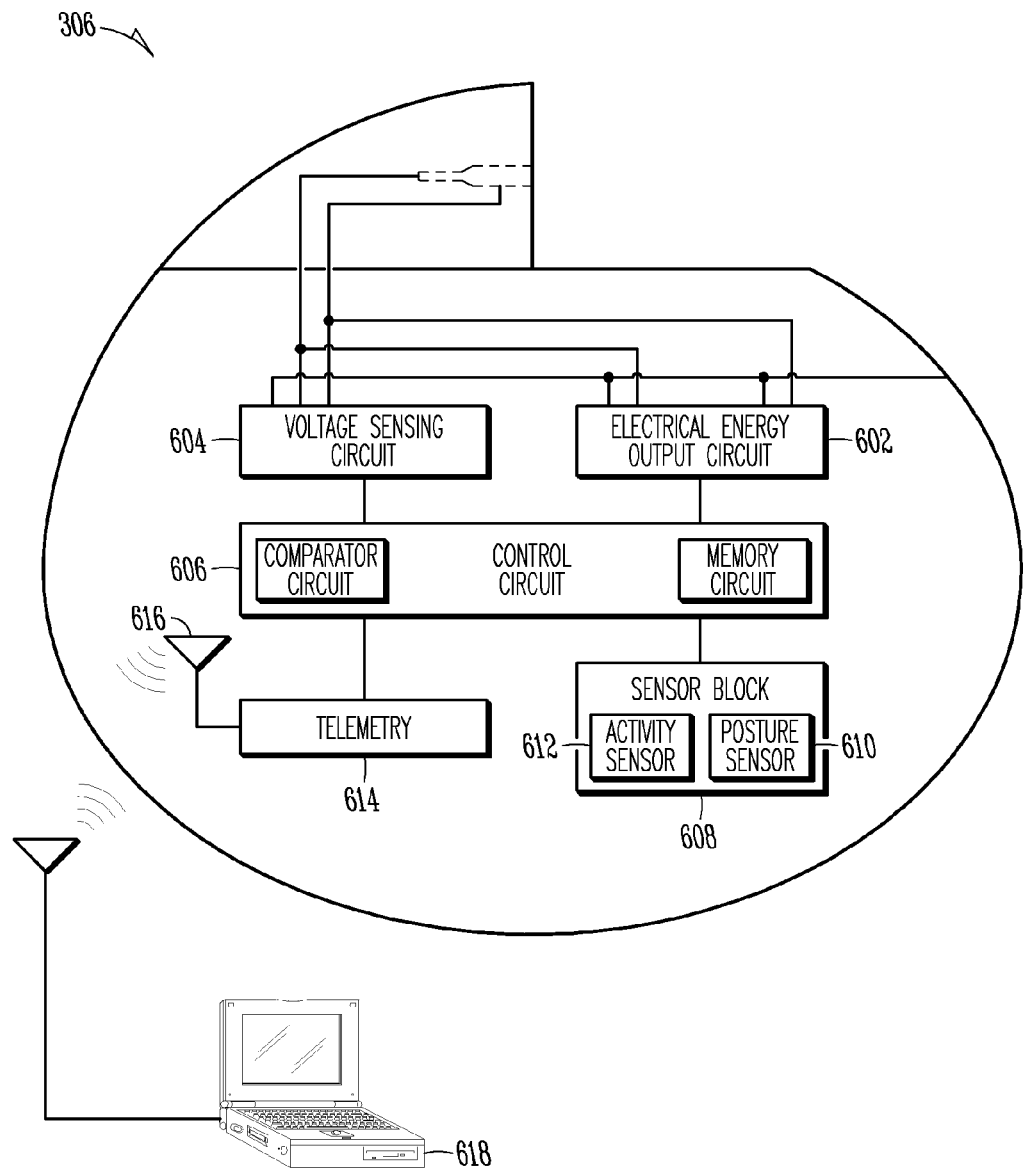
FIG. 6 is a block diagram illustrating one or more components of an implantable medical device, which may be used in a system including an electrode configuration providing negative sensitivity regions within a subject.

FIG. 6 illustrates an exemplary block diagram circuit representation of an IMD 306, such as the IMD of FIGS. 3 and 4. IMD 306 includes circuits for, among other things, delivering an electrical energy stimulus, measuring a resulting voltage, and communicating with one or more external devices. An electrical energy output circuit 602 includes a pulse generator, which may generate a pulse and deliver such pulse between two or more electrodes (e.g., 310, 312 (FIG. 4)), such as a constant current pulse or a constant voltage pulse, for example. This creates a lead field (e.g., 402 (FIG. 4)) in the body of a subject. A responsive voltage may be measured using a voltage sensing circuit 604. In one example, voltage sensing circuit 604 is electrically coupled to two different electrodes (e.g., 420, 308 (FIG. 4)) than the electrodes used to deliver the electrical energy stimulus. In one such example, the electrodes used to measure the resulting voltage are positioned such the responsive lead field opposes the delivered lead field, thereby creating a negative sensitivity electrode configuration.

A control circuit 606 receives or contains information on the magnitudes of the electrical energy stimulus and the resulting measured voltage. An analog-to-digital (referred to as "A/D") converter may be used to translate such information into a digitized form used by the control circuit 606. A processing unit such as a microprocessor, microcontroller, or digital signal processor within control circuit 606 may then use information about the electrical energy stimulus and resulting voltage to calculate a fluid volume indicative signal. In one example, the fluid volume indicative signal is calculated solely using information about the resulting measured voltage.

In another example, the fluid volume indicative signal is calculated using a product of the resulting measured voltage and the introduced current. In this case, the monitored quantity may be thought of as a partial measure of dissipated power in, for example, the thorax, since power dissipated by a resistive load is the product of the current flowing through it times the voltage it has. In the example of left lung 304 located in a negative sensitivity arrangement, the more edema fluid the lung has, the more the voltage in limbs (for example) increases, such that the power available and measured elsewhere in the body will consequently be increased as well. This increase in power appearing on the body can be monitored using, for example, internal can electrode 312 and right ventricular electrode 308 (see FIG. 7) to measure the power appearing in a substantial portion of the subject's thorax. Using the power to monitor fluid status takes advantage of the synergistic increases in injected current and resultant voltage that occur when edema fluid appears in a targeted organ. The multiplication of these two synergistic quantities amplifies the measurement signal of the developing edema, yielding a more sensitive system to the fluid in the targeted organ.

As discussed above, when the fluid within a region of a subject increases, the resulting measured voltage also increases (assuming a negative sensitivity electrode configuration). Thus, simple monitoring of a resulting measured voltage change in response to a delivered voltage pulse may be used to monitor fluid and assess whether pulmonary edema is present, and if so, a degree of the edema. Thus, the present IMD 306 need not contain a dedicated current reference circuit to ensure a constant current is delivered between the two or more stimulus electrodes as is often the case in impedance-based fluid monitoring systems. Because such current information is not critical for fluid monitoring purposes according to the present systems and methods (which relate to a negative sensitivity electrode configuration), a voltage source stimulus can be used instead of a current source stimulus, if desired.

Control block 606 may additionally include read-only memory (referred to as "ROM"), random-access memory (referred to as "RAM"), flash memory, EEPROM memory, and the like, which may store instructions that may be executed by the processing unit, as well as digital-to-analog (referred to as "D/A") converters, timers, counters, filters, switches, etc. Electrical energy stimulus and resulting measured voltage values may also be stored in the memory.

Information from a different source, such as sensor block 608, may be use to adjust the relationship between the measured resulting voltage and the amount of fluid in the subject. In one example, a posture sensor 610 may provide patient orientation or posture information to control block 606, allowing posture compensation to be included in the assessment of fluid build-up. Because organs, such as the lungs, and excess fluid in the thorax and lungs 304 (FIG. 3) shift with posture changes due to gravity, measured resulting voltage may vary as a subject assumes different positions. In another example, an activity sensor 612 may also provide information to control block 606.

A telemetry block 614 may communicate wirelessly using radio frequency (referred to as "RF") transmissions over an antenna 616 with a similarly wirelessly equipped external device 618. External device 618 may be a computer, a home station device, a wearable device, an external weight scale, or any other appropriate device that may be used to program IMD 306 or retrieve information from the IMD, such as information about the electrical energy stimulus or the resulting voltage sensed. One example of a suitable external weight scale for use with the present systems and methods is discussed in commonly assigned Belalcazar, U.S. patent application Ser. No. 11/419,120, entitled "MONITORING FLUID IN A SUBJECT USING A WEIGHT SCALE," filed May 18, 2006, which is hereby incorporated by reference in its entirety. Such communication can be used to provide the subject or a caregiver with an alert of a fluid increase indicative of pulmonary edema or CHF decompensation. Information about the subject's fluid status may also be used to titrate cardiac resynchronization or other therapy to the subject, where such therapy could be any therapy used to treat fluid accumulation or to regulate cardiovascular function.

Figure 7:
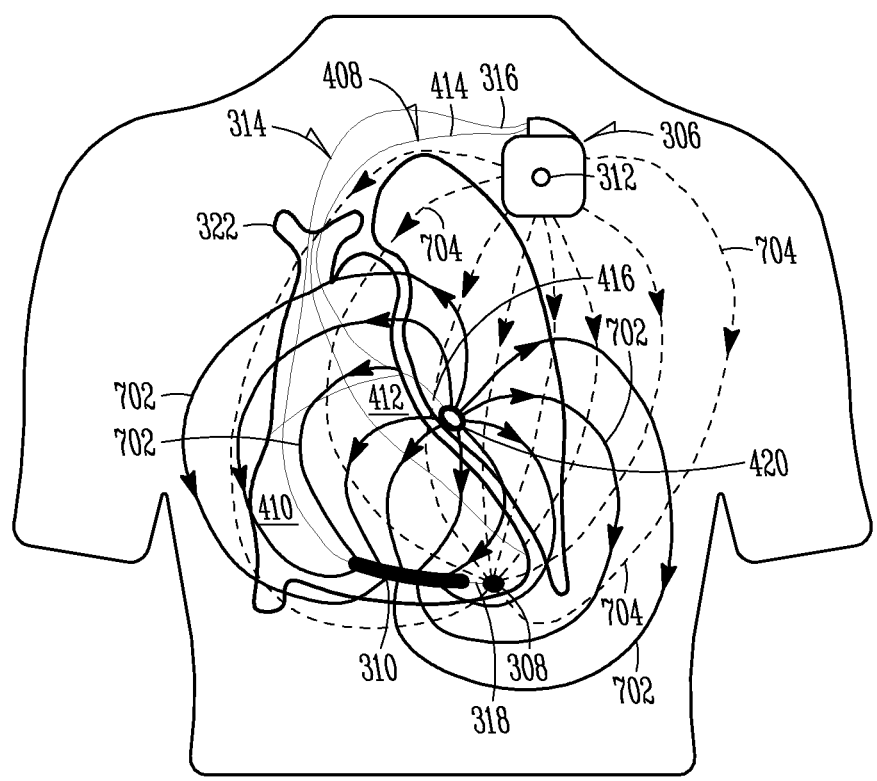
FIG. 7 is a perspective view illustrating a portion of an exemplary system adapted to monitor thoracic fluid in a subject and opposing lead fields associated with a negative sensitivity electrode configuration.

FIG. 7 illustrates another exemplary negative sensitivity electrode arrangement. In this example, an implantable apparatus includes an IMD 306, a first lead 314, and a second lead 408. First lead 314 extends from a lead proximal end 316, where it is coupled to IMD 306, to a lead distal end 318 disposed within, over, or about a heart 322 (such as a right ventricle 410) and thereby provides at least one conductive path from IMD 306 to the right ventricle. Second lead 408 extends from a lead proximal end 414 to a lead distal end 416 disposed within, over, or about heart 322 (such as a left ventricle 412) and thereby provides at least one conductive path from IMD 306 to the left ventricle. As shown, but as may vary, first lead 314 includes two (implanted) electrodes 308, 310 near lead distal end 318, second lead 414 includes one (implanted) electrode 420 disposed near lead distal end 416, and a housing 312 or header of IMD 306 acts as a fourth (implanted) can electrode by being conductive or at least partial conductive.

In this way, when IMD 306 provides an electrical energy stimulus (e.g., a constant voltage source given by, for example, a leading edge part of an applied pacing pulse via electrical energy output circuit 602 (FIG. 6)) and electrodes 420 and 310. This creates a lead field 702. A responsive voltage may be measured (i.e., sensed) using electrodes 308 and electrode 312, which have an associated lead field 704. In FIG. 4, the lead field associated with the electrical energy stimulus electrodes 420, 310 is in an opposite direction to the lead field associated with the resulting voltage measurement electrodes 308, 312.

Figure 8:
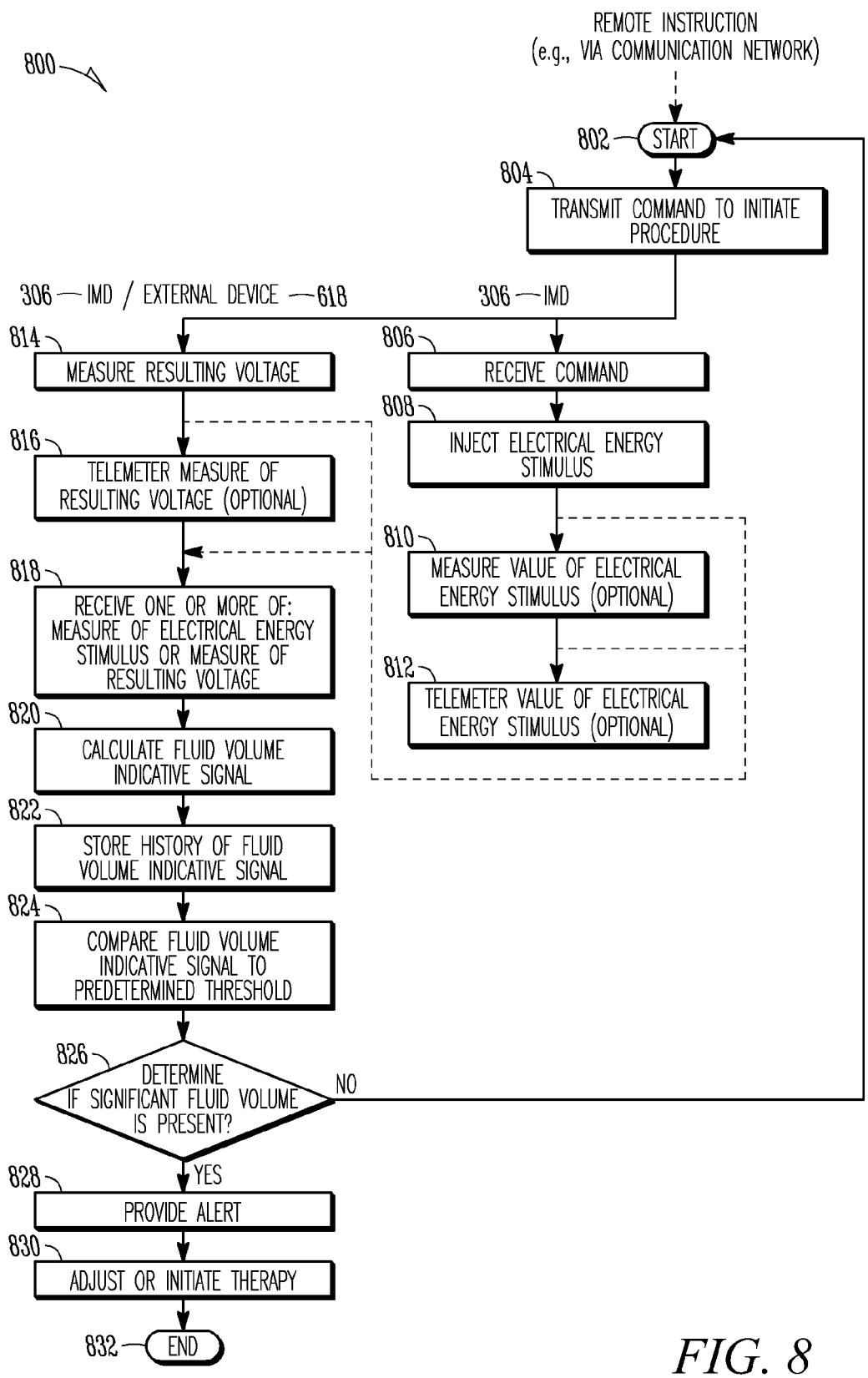
FIG. 8 is a flow chart illustrating an exemplary method providing monitoring of fluid in a region of a subject.

FIG. 8 illustrates a flow chart of an exemplary method 800 of monitoring fluid in a region of a subject, such as a thoracic region 302 (FIG. 3). The steps of method 800 may be performed solely by an IMD 306 or cooperatively using the IMD and one or more external devices 618, such as a computer, a home station device, or a weight scale. In one example, method 800 starts at 802, when a caregiver (remotely) transmits an instruction via a communication network to monitor fluid status within the subject. Upon receiving authorization, home station device 618, for example, transmits a command to IMD 306 to initiate the fluid monitoring procedure at 804.

At 806, IMD 306 receives the command and proceeds to inject an electrical energy stimulus, at 808, across a subject's thoracic region (e.g., by applying a pacing voltage between two electrodes). At 810, the injected stimulus is optionally measured by IMD 306. At 812, the measured value of the injected stimulus is optionally telemetered to an external device 618 for processing or storing within a memory.

At 814, a resulting voltage is measured by an external device, such as a weight scale device, or by IMD 306. Optionally, at 816, the measured value of the resulting voltage is telemetered from IMD 306 to an external device or is telemetered from an external device to IMD 306, depending on where such measurement is taken (i.e., internally or externally) and where processing of such measurement will take place. At 818, the measure of the injected stimulus or the resulting voltage is optionally received.

At 820, a processing unit integrated with IMD 306 or integrated with an external device calculates a fluid indicative signal using information about the resulting voltage signal, or by using information about the resulting voltage signal and about the injected stimulus. At 822, the calculated fluid indicative signal may be stored in a memory. At 824, the calculated fluid indicative signal may be compared to one or more other calculated fluid indicative signals to detect a change in a fluid. Alternatively or additionally, the calculated fluid indicative signal may be compared to a predetermined specified threshold value to determine whether a specified change in fluid amount has occurred, at 826. Other statistical techniques, histogram techniques, etc. may also be used to recognize a change in fluid status. Based on the operation at 826, an alert may be provided at 828 if it is determined that a specified amount of fluid exists within the subject's thoracic region. At 830, a therapy is adjusted or initiated in response to the operation at 826. Such therapy may be provided in a number of ways, such as cardiac resynchronization therapy, pacing therapy, cardioverter-defibrillator therapy, cardiac rhythm management therapy, dietary therapy, or diuretics. In this example, but as may vary, method 800 concludes at or before 832.

CONCLUSION

Pulmonary edema is a serious medical condition in which an excessive amount of fluid accumulates in a subject's thoracic region, such as the lungs. This condition may (and oftentimes does) result from heart failure. If it exists, pulmonary edema requires immediate care. While it can sometimes prove fatal, the outlook for subjects possessing pulmonary edema can be good upon early detection and prompt treatment.

Advantageously, the present systems and methods may provide enhanced and more simple monitoring of abnormal fluid build-up in the thoracic region, and thus may provide more timely and cost effective detection of thoracic fluid build-up, all in the confines of one's home—without having to make an office appointment or traveling thereto. Such detection is made possible by, among other things, internally injecting an electrical energy stimulus through the thoracic region, and calculating a fluid volume indicative signal. Unlike previous fluid monitoring systems, calculation of the fluid volume indicative signal according to the present systems and methods does not require determining impedances or using a constant current source for the injected electrical energy. Rather, the fluid volume indicative signal can be found by delivering a test voltage stimulus that is, for example, constant over a time greater than a few second, and using information about the resulting voltage signal, or by using information about the introduced signal and the resulting voltage signal. The current injection stimulus need not be specific to the monitoring sub-system, but can be the common pacing pulse of a cardiac rhythm device. This aspect of the invention simplified the circuit of the implanted device.

While the majority of this patent document discusses the monitoring of fluid in a thoracic region of subject, the present subject matter is not so limited. The fluid monitoring techniques recited herein may be used throughout a subject's body, provided an electrical energy stimulus may be injected and a resulting voltage signal measured. As used herein, an IMD may include, but is not limited to, cardiac rhythm management (referred to as "CRM") devices such as pacemakers, cardioverters, defibrillators; cardiac resynchronization therapy (referred to as "CRT") or coordination devices, drug delivery systems, or any other device or combination of devices adapted to deliver an electrical stimulation pulse (e.g., a pacing pulse). Additionally, the current injection and voltage measurement electrode pairs discussed herein may be exchanged (i.e., swapped) yielding equivalent measurements (as supported by the Helmholtz theorem of reciprocity). For instance, an electrode pair used to inject a current in one example, may be used to measure a resulting voltage in another example. Likewise, an electrode pair used to measure the resulting voltage in one example, may be used to inject the current in another example.

It is to be understood that the above description is intended to be illustrative, and not restrictive. For example, the above-described embodiments (or aspects thereof) may be used in combination with each other. Many other embodiments will be apparent to those of skill in the art upon reviewing the above description. The scope of the present systems and methods should, therefore, be determined with reference to the appended claims, along with the full scope of legal equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, assembly, article, or method that includes elements in addition to those listed after such a term in a claim are still deemed to fall within the scope of that claim. Moreover, in the following claims, the terms "first," "second," and "third," etc.

are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A system to monitor fluid in a region of interest of a subject, the system comprising:
   a test electrical energy delivery circuit configured to deliver a test stimulus between a first electrode at a first originating location and a second electrode at a first terminating location, the test electrical energy delivery circuit configured to create a first lead field between the first and second electrodes;
   a responsive voltage sensing circuit configured to receive a responsive voltage between a third electrode at a second originating location and a fourth electrode at a second terminating location, the third and fourth electrodes configured to receive the responsive voltage between the second originating location and the second terminating location, the responsive voltage sensing circuit configured to create a second lead field between the third and fourth electrodes; and
   a control circuit configured to:
      control delivery of the test stimulus by the test electrical energy delivery circuit;
      receive information about the responsive voltage from the responsive voltage sensing circuit; and
      determine a fluid indication based on an increase in the responsive voltage relative to the test stimulus being correlated to an increase in fluid in the region of interest when the first, second, third, and fourth electrodes are configured in a negative sensitivity configuration, with the first and second lead fields having opposing field directions in the region of interest.

2. The system of claim 1, further including the first, second, third, and fourth electrodes.

3. The system of claim 2, wherein the first electrode is configured for location at a left pectoral region of a thorax of the subject, the second electrode is configured for location at a right ventricle of a heart of the subject, the third electrode is configured for location at a left ventricle of the heart of the subject, and the fourth electrode is configured for location at the right ventricle of the heart of the subject.

4. The system of claim 2, wherein the region of interest is located between the first originating location and the second originating location.

5. The system of claim 1, including a memory circuit configured to store the received responsive voltage.

6. The system of claim 1, including a comparator circuit adapted to determine a specified fluid status event based on a comparison of the responsive voltage to a specified threshold value.

7. The system of claim 1, wherein the control circuit is configured to provide a non-impedance signal indicative of fluid status in the region of interest of the subject using the received responsive voltage.

8. The system of claim 1, wherein the test stimulus includes a constant test voltage.

9. The system of claim 1, wherein the region of interest of the subject includes a left lung region of the subject.

10. The system of claim 1, wherein the control circuit is configured to determine the increase in fluid in the region of interest solely using the received responsive voltage.

11. The system of claim 1, wherein the responsive voltage sensing circuit is configured to receive the responsive voltage in response to the delivered test stimulus.

12. A method to monitor fluid in a region of interest of a subject, the method comprising:
    delivering a test stimulus between a first electrode at a first originating location and a second electrode at a first terminating location, creating a first lead field between the first and second electrodes;
    measuring a responsive voltage between a third electrode at a second originating location and a fourth electrode at a second terminating location, creating a second lead field between the third and fourth electrodes, wherein the first, second, third, and fourth electrodes are configured in a negative sensitivity configuration that includes opposing field directions of the first and second lead fields in the region of interest; and
    determining, using a control circuit, a fluid indication based on an increase in the responsive voltage relative to the test stimulus being correlated to an increase in fluid in the region of interest when the first, second, third, and fourth electrodes are configured in said negative sensitivity configuration, with the first and second lead fields having opposing field directions in the region of interest.

13. The method of claim 12, including monitoring the fluid indication for an increase in fluid volume.

14. The method of claim 13, including generating an alert in response to a specified detected increase in the fluid volume.

15. The method of claim 12, including adjusting a therapy to the subject using the fluid indication.

16. The method of claim 12, wherein the delivering the test stimulus between the first electrode at the first originating location and the second electrode at the first terminating location includes delivering the test stimulus originating in a left pectoral region of a thorax of the subject and terminating the test stimulus in a right ventricle of a heart of the subject; and
    wherein the measuring the responsive voltage between the third electrode at the second originating location and the fourth electrode at the second terminating location includes measuring from a left ventricle of the heart of the subject to the right ventricle of the heart of the subject.

17. The method of claim 12, wherein the delivering the test stimulus includes delivering a constant test voltage.

18. The method of claim 12, wherein the determining the fluid indication includes determining the fluid indication solely using the increase in the measured responsive voltage.

19. The method of claim 12, wherein the region of interest is located between the first originating location and the second originating location.

* * * * *